US00PP32159P3

(12) United States Plant Patent
Takano

(10) Patent No.: US PP32,159 P3
(45) Date of Patent: Sep. 8, 2020

(54) APPLE TREE NAMED 'TAKANO 7GO'

(50) Latin Name: ***Malus* Mill.**
Varietal Denomination: TAKANO 7GO

(71) Applicant: Tsuyoshi Takano, Oshu-shi (JP)

(72) Inventor: Takao Takano, Oshu (JP)

(73) Assignee: Tsuyoshi Takano, Oshu-shi (JP)

( * ) Notice: Subject to any disclaimer, the term of this patent is extended or adjusted under 35 U.S.C. 154(b) by 0 days.

(21) Appl. No.: 15/932,601

(22) Filed: Mar. 23, 2018

(65) Prior Publication Data

US 2019/0150337 P1 May 16, 2019
US 2020/0196501 P9 Jun. 18, 2020

(30) Foreign Application Priority Data

Nov. 11, 2017 (JP) ..... 32562

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
See application file for complete search history.

(56) References Cited

U.S. PATENT DOCUMENTS

PP11,077 P 10/1999 Yu-Lin
PP11,511 P 9/2000 Kudo

*Primary Examiner* — Susan McCormick Ewoldt
(74) *Attorney, Agent, or Firm* — Oblon, McClelland, Maier & Neustadt, L.L.P.

(57) ABSTRACT

A new and distinct variety of apple tree named 'TAKANO 7GO' having a longer common storage duration of about one month even at an average temperature of about 20-25° C., balanced sweetness and acidity of the fruit, higher firmness of the flesh, and earlier harvest time (for example, from late August to early September in Japan).

6 Drawing Sheets

The botanical name of the novel apple tree variety is *Malus* Mill.

The novel variety of the *Malus* Mill is hereinafter referred to by the variety denomination: 'TAKANO 7GO'.

CROSS-REFERENCE TO RELATED APPLICATIONS

This application claims priority to Japanese Variety Registration Application No. 32562 filed Nov. 1, 2017, which is incorporated by reference herein as if set forth in its entirety.

BACKGROUND OF THE INVENTION

The present invention relates to a new and distinct variety of apple tree botanically classified as *Malus* Mill. and hereinafter referred to by the name 'TAKANO 7GO'.

The new variety is a product of a planned breeding program conducted during a period from May 2006 to September 2017 by the inventor, Oshu-shi, Iwate, Japan, in which the *Malus* Mill. variety 'Shinano Gold' (female parent; Japanese Variety Registration No. 7328, registered Aug. 11, 1999) was crossed with the *Malus* Mill. variety 'TAKANO 1GO' (male parent) which is also known as the name 'Beni Roman' (Japanese Registered Trademark No. 5128504, registered Apr. 11, 2008) in Japan. The objective of the breeding program was to create new apple trees that produce fruits having long common storage duration and firm flesh, different from those of the parents and known similar varieties.

SUMMARY OF THE INVENTION

The new and distinct variety 'TAKANO 7GO' has a longer common storage duration of about one month even at an average temperature of about 20-25° C., balanced sweetness (about 14.5-15 (Brix %)) and acidity (about 0.33 g/100 ml) of the fruit, higher firmness of the flesh (about 15.3 lbs.), and earlier harvest time (for example, late August to early September in Japan), and, as described below, is distinct from: the known variety 'Shinano Gold' (female parent) that was produced by crossing the *Malus* Mill variety 'Golden Delicious' which is a classic American apple variety and is also well known in Japan with the known variety 'Senshu' (Japanese Variety Registration No. 42, registered Mar. 31, 1980), the known *Malus* Mill. variety 'TAKANO 1GO' (male parent, Japanese Variety Registration No. 20599, registered Mar. 15, 2011) that was produced by crossing the known *Malus* Mill variety 'Shinano Red' (Japanese Variety Registration No. 5867, registered Dec. 5, 1997) with the known *Malus* Mill. variety 'Sansa' (Japanese Variety Registration No. 1565, registered Mar. 5, 1988); and the *Malus* Mill. variety 'Tsugaru' well known in Japan.

BRIEF DESCRIPTION OF THE DRAWINGS

The accompanying colored photographs (FIGS. 1-6) show typical flower, fruit, and leaf characteristics for the new *Malus* Mill. apple tree variety, 'TAKANO 7GO'. Colors shown are as accurate as can be reasonably reproduced by photographic means. In some cases, the color might differ slightly from the colors of 'RYOKU NH-13' described herein.

DETAILED BOTANICAL DESCRIPTION

Figure 1:
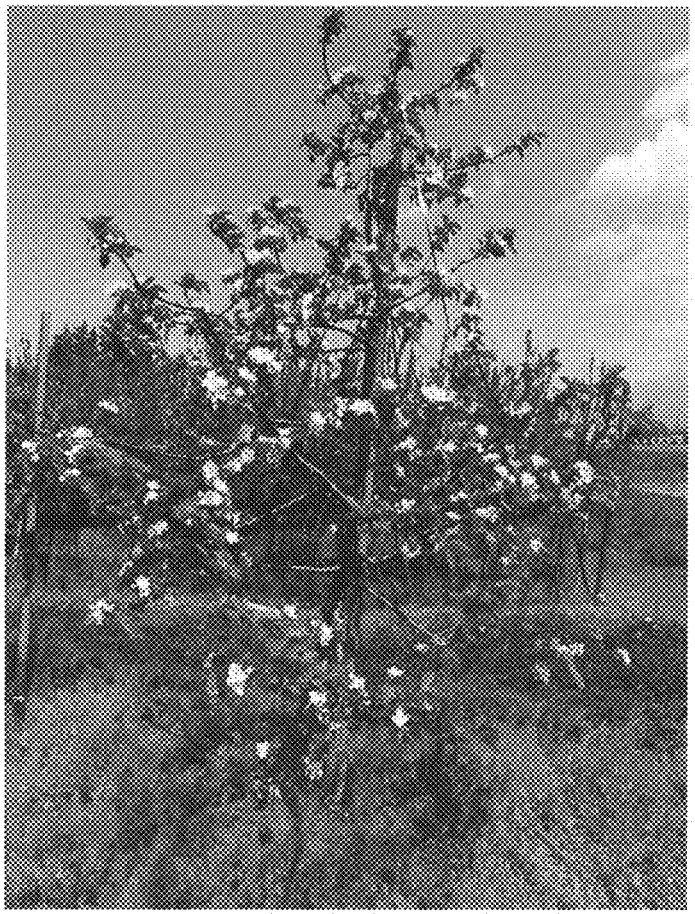
FIG. 1 shows a tree (about 9 years old) of 'TAKANO 7GO' in bloom.
Figure 2:
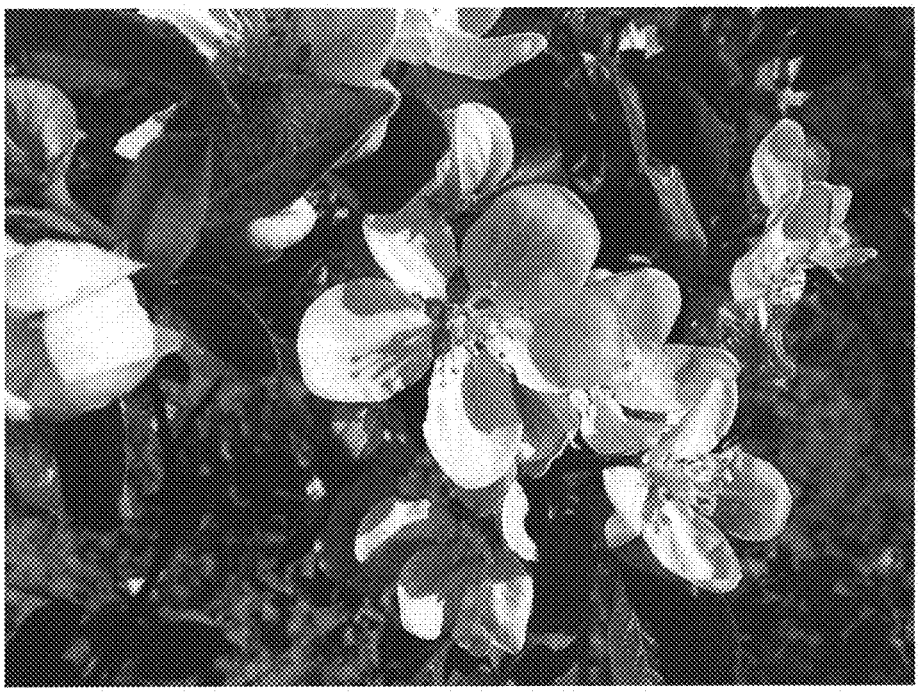
FIG. 2 shows a close-up view of the flowers of 'TAKANO 7GO'.
Figure 3:
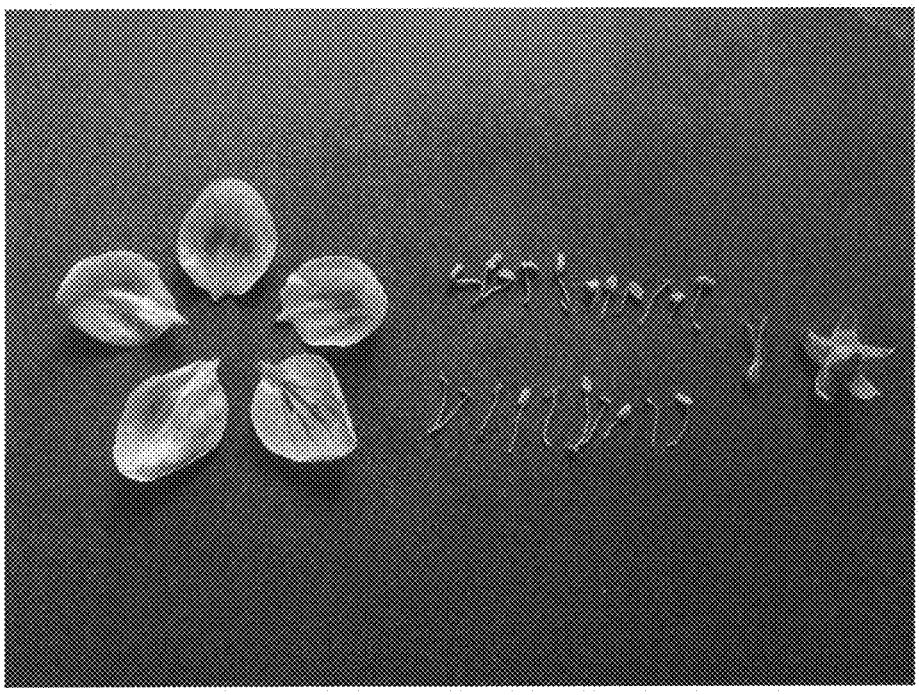
FIG. 3 shows petals, pistil, stamens and sepal of the flower of 'TAKANO 7GO'.
Figure 4:
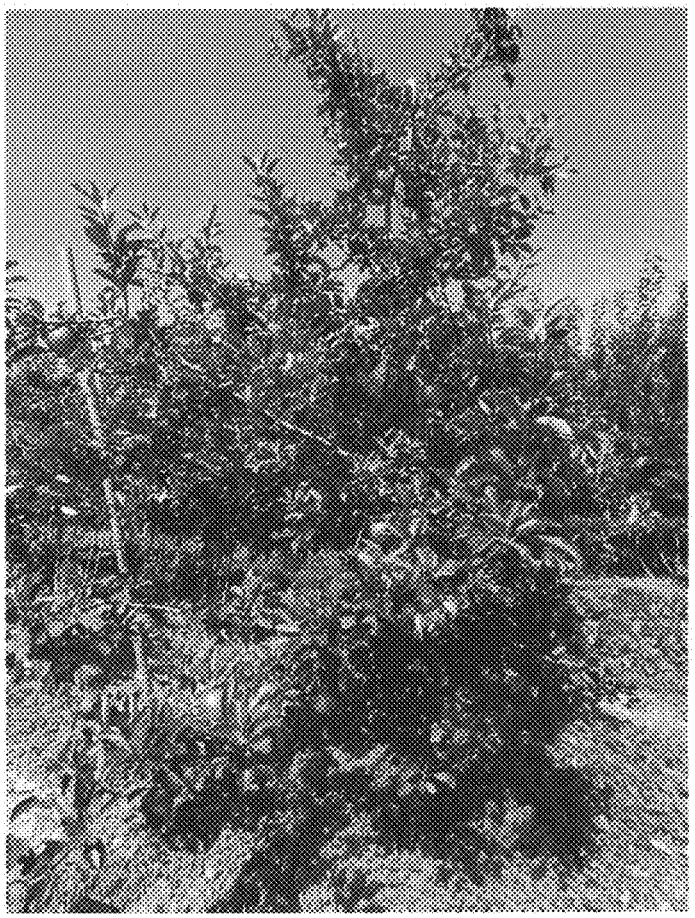
FIG. 4 shows a tree, fruits, and leaves of 'TAKANO 7GO'.
Figure 5:
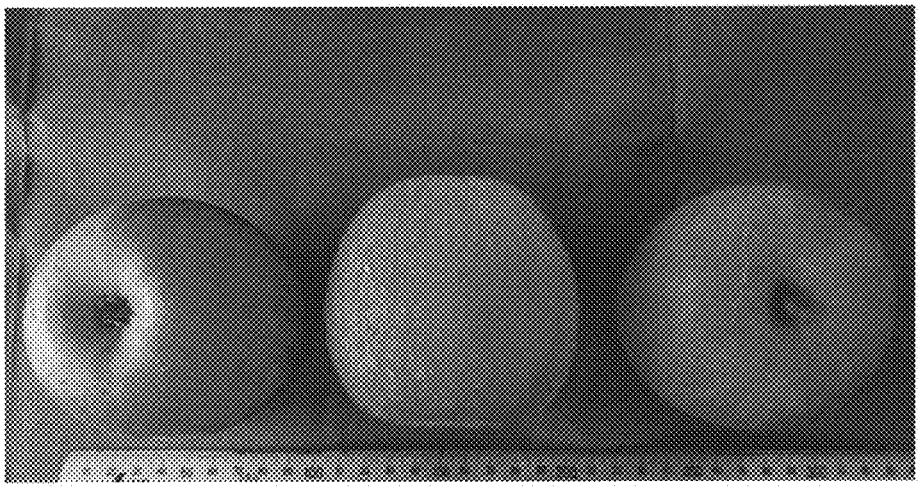
FIG. 5 shows the shape and diameter of the whole fruit of 'TAKANO 7GO'.
Figure 6:
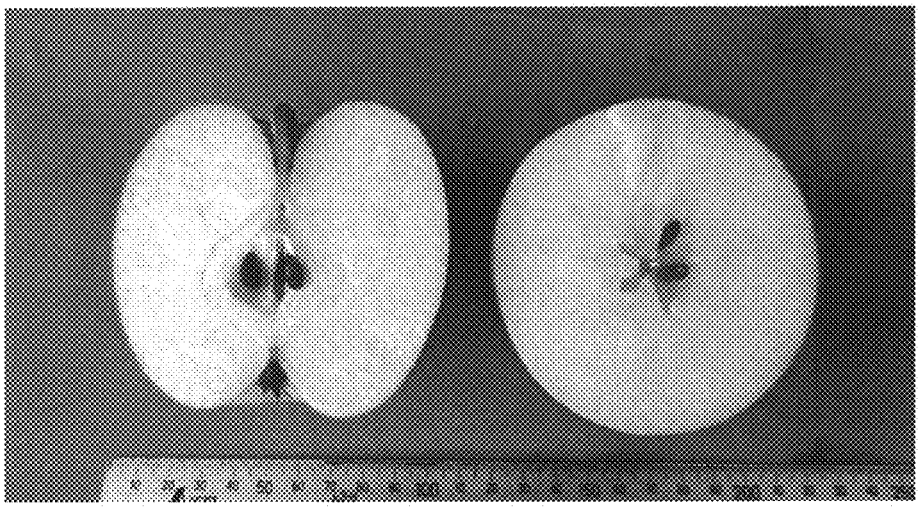
FIG. 6 shows a longitudinal cross-sectional view of the fruit of 'TAKANO 7GO'.

The new variety 'TAKANO 7GO' has characteristics as described below, compared with the parent varieties and similar varieties. (see TABLEs 1, 2 and 3).

TABLE 1

Partial characteristics of 'TAKANO 7GO'

| Characteristic | State |
|---|---|
| Tree: type | ramified |
| Tree: habit | spreading |
| Fruit: height | medium, about 8 cm on average |
| Fruit: general shape | ovoid |
| Fruit: relative area of overcolor | very large |
| Fruit: hue of overcolor, with bloom removed | orange red (RHS, approximately N34A) |
| Fruit: intensity of stripes of overcolor | weak |
| Fruit: color of flesh | yellow white (RHS, approximately 158D) |
| Time of beginning of flowering | medium |
| Time of harvest | early |

The variety 'Shinano Gold', a female parent, has the characteristics of that the skin color is yellow (RHS Yellow Group approximately 6C) when harvested, the sweetness of flesh is high (about 15.3 (Brix %)), the acidity of flesh is medium (about 0.45.g/100 ml), the firmness or food texture (i.e., mouthfeel) of flesh is firm (about 15.5 lbs.), and the time of harvest is late, specifically late October in Iwate, Japan.

The variety 'TAKANO 1GO', a male parent, has the characteristics that the skin color is red (RHS Red Group approximately 46B) when harvested, the color of flesh is yellow white (RHS Yellow-White Group approximately 158D), the acidity of flesh is about 0.50 g/100 ml, the firmness of flesh is about 16.0 lbs., the time of harvest is very early, specifically mid of August at Iwate, Japan, and the common storage duration is short (about 4-10 days in August at Iwate, Japan).

On the other hand, the new and distinct variety 'TAKANO 7GO' has the characteristics described in TABLE 1 above and TABLEs 2 and 3 below, especially that the time of harvest is from late August to early September at Iwate, Japan and the common storage duration is long (about one month even in the period late August to early September at Iwate, Japan (average temperature about 20-25° C.)) substantially without making the flesh soft and thus very superior to any known variety produced in Japan (normally up to about 10 days), that the skin color of the fruit is orange red (RHS Orange-Red Group approximately N34A) when harvested, and the color of the flesh is yellow white (RHS Yellow-White Group approximately 158D) and the firmness of the flesh is firm (about 15.3 lbs.), and that the sweetness of the fruit is about 14.5-15 (Brix %) and is higher than the sweetness of known fruits like 'Beni Roman' (i.e. the variety 'TAKANO 1GO') (about 13 (Brix %) and 'Sansa' (about 13-14 (Brix %)), and the acidity of the flesh is medium (about 0.33 g/100 ml), while having balanced sweetness and acidity and higher firmness of the flesh. Furthermore, in the new and distinct variety 'TAKANO 7GO', the leaves are arranged alternatively on the stem with one leaf per node in a straight line.

TABLE 2

Comparison of characteristics between the new variety and similar varieties

| | Varieties | | |
|---|---|---|---|
| Characteristic | TAKANO 7GO | Sansa (not patented)*1 | Tsugaru (not patented)*1) |
| Stripes of overcolor | weak | absent | — |
| Duration of common storage (at about 20-25° C.) | long, about 1 month | slightly short, 10 days or less | slightly short, 10 days or less |
| Fruit firmness of flesh | firm, about 15.3-16.0 lbs. | slightly firm, about 13.8 lbs | soft, about 13.0 lbs |

*1)'Sansa' and 'Tsugaru' are similar to 'TAKANO 7GO' in their harvest time.

The following detailed botanical description of 'TAKANO 7GO' apple tree is based an survey (or observations) made during the period between August 2013 and September 2017 at Oshu-shi, Iwate, Japan. All colors are described according to The Royal Horticultural Society Colour Chart. It should be understood that the characteristics described will vary somewhat depending upon cultural practices and climate conditions and will also vary depending upon location and season. Quantified measurements are generally expressed as an average of measurements taken from individual trees of 'TAKANO 7GO' unless otherwise noted; however, the measurements of any individual plant or any group of plants of 'TAKANO 7GO' may vary from the stated average.

Classification:

*Botanical.—Malus* Mill.

Parentage:

*Female parent.—Malus* Mill. variety 'Shinano Gold' (Japanese Variety Registration No. 7328, registered Aug. 11, 1999).

*Male parent.—Malus* Mill. variety 'TAKANO 1GO' (male parent; Japanese Variety Registration No. 20599, registered Mar. 15, 2011).

Propagation: Typically by grafting on JM1 (Japanese Variety Registration No. 7443, registered Sep. 21, 1999) rootstock; and the good time of grafting is a period of mid to late March at Iwate, Japan.

Flowering-beginning time: Typically early May at Iwate, Japan.

Harvest time: Typically a period between late August and early September at Iwate, Japan.

Plant description: See TABLE 3 below indicating characteristics of 'TAKANO 7GO' compared with the similar variety 'Sansa' (Japanese Variety Registration No. 1565, registered Mar. 5, 1988).

TABLE 3

Characteristics of 'TAKANO 7GO' compared with 'Sansa'

| Characteristic | 'TAKANO 7GO' | 'Sansa' |
|---|---|---|
| Tree: vigor | medium | medium |
| Tree: type | ramified | ramified |
| Only varieties with ramified tree type: Tree: habit | spreading | spreading |
| Tree: type of bearing | on spurs and long | on spurs and long |
| One-year-old shoot: thickness | medium, about 4.5 mm | medium, about 4.5 mm |
| One-year-old shoot: length of internode | short, about 2.7 cm | medium, about 3.3 cm |
| One-year-old shoot: color on sunny side | moderate brown (RHS Brown Group 200C) | light brown (RHS Grey-Brown Group N199C) |
| One-year-old shoot: pubescence (on distal half of shoot) | densely pubescent | medium |
| One-year-old shoot: number of lenticels | many (the number of lenticels, not determined.) | medium |
| Leaf blade: attitude in relation to shoot | upwards | upwards |
| Leaf blade: length | medium, about 9.5 cm | medium, about 9.8 cm |
| Leaf blade: width | narrow, about 5.8 cm | narrow, about 5.9 cm |
| Leaf blade: ratio length/width | large, about 1.63 | large, about 1.66 |
| Leaf blade: intensity of green color | medium | medium |
| Leaf blade: incisions of margin (upper half) | serrate type 1 | bicrenate |
| Leaf blade: pubescence on lower side | densely pubescent | medium |
| Leaf blade: pubescence on upper side | absent | — |
| Petiole: length | medium, about 2.8 cm | long, >2.8 cm |
| Petiole: color | RHS Yellow-Green Group146C | — |
| Petiole: diameter | about 2 mm on average | — |
| Petiole: extent of anthocyanin coloration from base | medium | medium |
| Flower: predominant color at balloon stage | strong pink (RHS Red Group 50C) | light pink (RHS Red Group 50D) |
| Flower: diameter with petals pressed into horizontal position | medium, about 5.5 cm on average | medium, about 5.8 cm on average |
| Flower: arrangement of petals | moderately overlapping | moderately overlapping |
| Flower: petal length | about 2.5-3.0 cm on average | — |
| Flower: petal width | about 1.7-2.1 cm on average | — |
| Flower: petal color on the upper side | predominantly White Group RHS N155B to N155D and partly Red-Purple Group RHS 65B to 65C | — |
| Flower: petal color on the lower side | predominantly RHS White Group N155B to N155D and partly Red-Purple Group RHS N74B to N74C | — |
| Flower: shape of petal apex | rounded | — |
| Flower: shape of petal base | rounded | — |
| Flower: petal texture | soft and fragile | — |

TABLE 3-continued

Characteristics of 'TAKANO 7GO' compared with 'Sansa'

| Characteristic | 'TAKANO 7GO' | 'Sansa' |
|---|---|---|
| Flower: the average number of petals | 5 | 5 |
| Flower: length of flower buds | about 1.5 cm on average | — |
| Flower: diameter of flower buds | about 1.3 cm on average | — |
| Flower: color of flower buds | RHS Red-Purple Group 63A to 63B | — |
| Flower: position of stigmas relative to anthers | same level | same level |
| Flower: fertility | cross-pollination | cross-pollination |
| Anthers: color | RHS Yellow Group 10A | — |
| Filaments: length | about 8-12 mm | — |
| Filaments: color | Blue-Green RHS 115A to 115B | — |
| Pistil: number | one (1) (the number of stigmas, 5) | — |
| Pistil: length | about 1.3 cm on average | — |
| Pistil: color | Yellow Green Group RHS 152C | — |
| Young fruit: extent of anthocyanin overcolor | medium | medium |
| Fruit: size | medium | medium |
| Fruit: height | medium, about 8.0 cm | medium, about 8.0 cm |
| Fruit: diameter | medium, about 8.0 cm | medium, about 7.8 cm |
| Fruit: ratio height/diameter | very small, 1.0 | small, 1.03 |
| Fruit: general shape | ovoid | conic |
| Fruit: ribbing | absent or weak | absent or weak |
| Fruit: crowning at calyx end | absent or weak | absent or weak |
| Fruit: size of eye | small (actual size, not determined.) | small |
| Fruit: length of sepal | medium | medium |
| Fruit: bloom of skin | absent or weak | absent or weak |
| Fruit: greasiness of skin | absent or weak | absent or weak |
| Fuit: surface texture of skin | smooth | medium |
| Fruit: ground color | whitish green | whitish green |
| Fruit: relative area of overcolor | very large | medium |
| Fruit: hue of overcolor-with bloom removed | RHS Orange Red approximately N34A | RHS Red Group approximately 46B |
| Fruit: intensity of overcolor | medium | medium |
| Fruit: pattern of overcolor | solid flush with weakly defined stripes | only solid flush |
| Fruit: width of stripes | medium (about 1.5-2.0 mm on average) | narrow (or absent) |
| Fruit: intensity of overcolor | weak | absent |
| Fruit: area of russet around stalk attachment | absent or small | medium |
| Fruit: area of russet on cheeks | absent or small | medium |
| Fruit: area of russet around eye basin | absent or small | large |
| Fruit: number of lenticels | many (about 5 per 1 $cm^2$ of equatorial portion) | medium |
| Fruit: size of lenticels | large (about 0.3 mm on average) | medium |
| Fruit: scarfskin | absent | absent |
| Fruit: length of stalk | short, about 1.8 cm | short, about 1.9 cm |
| Fruit: thickness of stalk | medium, about 2.5 mm | medium, about 2.4 mm |
| Fruit: depth of stalk cavity | medium, about 1.3 cm | medium, about 1.3 cm |

TABLE 3-continued

Characteristics of 'TAKANO 7GO' compared with 'Sansa'

| Characteristic | 'TAKANO 7GO' | 'Sansa' |
|---|---|---|
| Fruit: width of stalk cavity | medium,about 3.7 cm | medium, about 3.8 cm |
| Fruit: depth of eye basin | medium, about 1.0 cm | medium, about 1.0 cm |
| Fruit: width of eye basin | medium, about 3.6 cm | medium, about 3.6 cm |
| Fruit: firmness of flesh | firm, about 15.3 lbs. | medium, about 13.8 lbs. |
| Fruit: color of flesh | RHS Yellow-White Group approximately 158D | RHS White Group approximately 155D |
| Fruit: sweetness of flesh | medium, about 14.6 (Brix %) | medium, about 13-14 (Brix %) |
| Fruit: acidity of flesh | medium, about 0.33 (g/100 ml) | medium, about 0.41 (g/100 ml) |
| Fruit: water-core of flesh | absent to very slight | absent to very slight |
| Fruit: shape of core | flat round, 2.4 × 2.4 (cm) | flat round, 2.6 × 2.6 (cm) |
| Fruit: aperture of locules (in transverse section) | moderately open | moderately open |
| Fruit: productivity (kg/tree) | Productivity: about 40 kg per tree | — |

TABLE 3-continued

Characteristics of 'TAKANO 7GO' compared with 'Sansa'

| Characteristic | 'TAKANO 7GO' | 'Sansa' |
|---|---|---|
| Time of beginning of flowering | medium | medium |
| Time of harvest | early | early |
| Duration of storage: common storage | long, about one month (August, Japan) | slightly short, 10 days or less (August, Japan) |
| Duration of storage: cold storage | long (about 3 months at 4° C.) | slightly short (about 20 days at 4° C.) |
| Resistance to: *Alternalia* blotch (*Alternalia mali* Roberts) | strong | strong |
| Tolerance to winter hardiness | strong | strong |
| Tolerance to drought/heat | strong | weak |

What is claimed is:

1. A new and distinct variety of *Malus* Mill. apple tree named 'TAKANO 7GO', as illustrated and described herein.

* * * * *